United States Patent
Guegler et al.

(10) Patent No.: US 6,703,239 B2
(45) Date of Patent: Mar. 9, 2004

(54) NUCLEIC ACID ENCODING A FUSION PROTEIN COMPRISING AN EIF-4E DOMAIN AND AN EIF-4G DOMAIN JOINED BY A LINKER DOMAIN

(75) Inventors: Karl Guegler, Menlo Park, CA (US); Ruoying Tan, Foster City, CA (US); Michael J. Rose, Palo Alto, CA (US)

(73) Assignee: Incyte Corporation, Palo Alto, CA (US)

(*) Notice: Subject to any disclaimer, the term of this patent is extended or adjusted under 35 U.S.C. 154(b) by 30 days.

(21) Appl. No.: 10/180,196

(22) Filed: Jun. 25, 2002

(65) Prior Publication Data

US 2003/0124562 A1 Jul. 3, 2003

Related U.S. Application Data

(62) Division of application No. 10/002,528, filed on Nov. 1, 2001, now Pat. No. 6,436,676, which is a division of application No. 09/799,645, filed on Mar. 5, 2001, now Pat. No. 6,369,199, which is a continuation of application No. 09/352,540, filed on Jul. 13, 1999, now Pat. No. 6,326,175.

(51) Int. Cl.[7] .................... C12N 5/10; C12N 1/00; C12N 15/62; C12N 15/63
(52) U.S. Cl. .................... 435/325; 435/243; 435/320.1; 435/419; 536/23.4
(58) Field of Search .................... 536/23.4; 435/325, 435/419, 243, 320.1

(56) References Cited

U.S. PATENT DOCUMENTS 5,219,989 A 6/1993 Sonemberg et al.

FOREIGN PATENT DOCUMENTS

| EP | 0 373 914 A2 | 6/1990 |
| WO | WO 98/08865 | 3/1998 |

OTHER PUBLICATIONS

Alphey, "PCR–Based Method for Isolation of Full–Length Clones and Splice Variants from cDNA Libraries," *Biotechniques*, (Mar. 1997) vol. 22(3):481–486.

Altmann et al., "mRNA Cap–Binding Protein: Cloning of the Gene Encoding Protein Synthesis Initation Factor eIF–4E from *Saccharomyces cerevisiae*," *Molecular and Cellular Biology*, (Mar. 1987), Vo. 7(3):998–1003.

Carninci et al., "High Efficiency Selection of Full–Length cDNA by Improved Biotinylated Cap Trapper," *DNA Research*, (1997), vol. 4(1):61–66.

Carninci et al., "High–Efficiency Full–Length cDNA Cloning by Biotinylated CAP Trapper," *Genomics*, (Nov. 1, 1996), vol. 37(3):327–336.

Edery, et al., "An Efficient Strategy to Isolate Full–Length cDNAs Based on an mRNA Cap Retention Procedure (CAPture)," *Molecular and Cellular Biology*, (Jun. 1995), vol. 15(6):3363–3371.

Haghighat, et al. "eIF4G Dramatically Enhances the Binding of EIF4E to the mRNA 5'–Cap Structure," *The Journal of Biological Chemistry*, (Aug. 29, 1997), vol. 272(35):21677–21680.

Hentze, "eIF4G: A Multipurpose Ribosome Adapter?" *Science*, (Jan. 24, 1997), vol. 275:500–502.

Okayama et al., "High–Efficiency Cloning of Full–Length cDNA," *Molecular and Cellular Biology*, (Feb. 1982) vol. 2(2):161–170.

Schmid et al., "A Procedure for Selective Full Length cDNA Cloning of Specific RNA Species," *Nucleic Acids Research*, (1987) vol. 15(10):3987–3996.

Seki et al., "High–Efficiency Cloning of Arabidopsis Full–Length cDNA by Biotinylated CAP Trapper," *The Plant Journal*, (Sep. 1998) vol. 15(5):707–720.

Sekine et al., "Synthesis of Full–Length cDNA using DNA–capped mRNA," *Nucleic Acids Symposium*, (1993), Series No. 29:143–144.

Suzuki et al., "Construction and Characterization of a Full Length enriched and a 5'–end–enriched cDNA Library," *Gene*, (Oct. 24, 1997) 200(1–2):149–156.

*Primary Examiner*—Terry McKelvey
(74) *Attorney, Agent, or Firm*—Incyte Corporation

(57) ABSTRACT

Methods and compositions are provided for producing full-length cDNA libraries. In the subject methods, full length first strand cDNAs are isolated using a fusion protein of an eIF-4E domain and an eIF-4G domain separated by a flexible linker. Also provided is the novel fusion protein employed in the subject methods, as well as nucleic acids encoding, and host cells capable of expressing, the same. Finally, kits for use in practicing the subject methods are provided. The subject invention finds use in a variety of applications in which full-length cDNA libraries are employed.

6 Claims, 2 Drawing Sheets

SEQUENCE LISTING

<160> NUMBER OF SEQ ID NOS: 7

<210> SEQ ID NO 1
<211> LENGTH: 30
<212> TYPE: DNA
<213> ORGANISM: Artificial Sequence
<220> FEATURE:
<223> OTHER INFORMATION: Synthesized Primer

<400> SEQUENCE: 1
gagatatacc atggcgactg tcgaaccgga      30

<210> SEQ ID NO 2
<211> LENGTH: 65
<212> TYPE: DNA
<213> ORGANISM: Artificial Sequence
<220> FEATURE:
<223> OTHER INFORMATION: Synthesized Primer

<400> SEQUENCE: 2
agttaagtgg gcacctggtc tttgagaatc ttctctggag acagcaacaa caaacctatt      60

-continued

```
tttag                                                              65

<210> SEQ ID NO 3
<211> LENGTH: 72
<212> TYPE: DNA
<213> ORGANISM: Artificial Sequence
<220> FEATURE:
<223> OTHER INFORMATION: Synthesized Primer

<400> SEQUENCE: 3
gctgtctcca gagaagattc tcaaagacca ggtgcccact taactgtgaa aaggagacgg    60
aaaattaagg ag                                                       72

<210> SEQ ID NO 4
<211> LENGTH: 65
<212> TYPE: DNA
<213> ORGANISM: Artificial Sequence
<220> FEATURE:
<223> OTHER INFORMATION: Synthesized Primer

<400> SEQUENCE: 4
gccggatcct cgagtcatta cttatcgtca tcgtccttgt aatcgccaag gttggcaaag    60
gatgg                                                               65

<210> SEQ ID NO 5
<211> LENGTH: 12
<212> TYPE: RNA
<213> ORGANISM: Homo sapiens
<220> FEATURE:
<221> NAME/KEY: polyA_signal
<222> LOCATION: (1)...(12)

<400> SEQUENCE: 5
aaaaaaaaaa aa                                                       12

<210> SEQ ID NO 6
<211> LENGTH: 13
<212> TYPE: DNA
<213> ORGANISM: Artificial Sequence
<220> FEATURE:
<223> OTHER INFORMATION: Synthesized Primer

<400> SEQUENCE: 6
tttttttttt ttt                                                      13

<210> SEQ ID NO 7
<211> LENGTH: 11
<212> TYPE: RNA
<213> ORGANISM: Homo sapiens

<400> SEQUENCE: 7
aaaaaaaaaa a                                                        11
```

NUCLEIC ACID ENCODING A FUSION PROTEIN COMPRISING AN EIF-4E DOMAIN AND AN EIF-4G DOMAIN JOINED BY A LINKER DOMAIN

CROSS-REFERENCE TO RELATED APPLICATIONS

This application is a Divisional of Prior U.S. patent application Ser. No. 10/002,528, filed Nov. 1, 2001, now U.S. Pat. No. 6,436,676 issued on Aug. 20, 2002 which application is a division of prior U.S. patent application Ser. No. 09/799,645, filed Mar. 5, 2001, issued Apr. 9, 2002 as U.S. Pat. No. 6,369,199; which application is a Continuation of prior U.S. patent application Ser. No. 09/352,540, filed Jul. 13, 1999, issued Dec. 4, 2001 as U.S. Pat. No. 6,326,175.

INTRODUCTION

1. Technical Field

The field of this invention is cDNA libraries.

2. Background of the Invention

A complementary DNA or cDNA is a deoxyribonucleic acid that contains the information coding for the synthesis of proteins, but lacks the intervening introns present in genomic DNA. The synthesis of cDNA, the use of cDNA and libraries of cDNA play a critical role in a variety of different application in biotechnology and related fields. Applications in which cDNAs and/or libraries thereof are employed include gene discovery, differential gene expression analysis, and the like. A variety of protocols have been developed to prepare cDNA and libraries thereof, where such methods are continually being modified.

In standard methods currently used for the preparation of cDNA libraries, the mRNA in the cell is isolated by virtue of the presence of a polyadenylated tail present at its 3' end which binds to a resin specific for this structure (oligo dT-chromatography). The purified mRNA is then copied into cDNA using a reverse transcriptase, which starts at the 3' end of the mRNA and proceeds towards the 5' end. Second strand synthesis is then performed. Linkers are added to the ends of the double stranded cDNA to allow for its packaging into virus or cloning into plasmids. At this stage, the cDNA is in a form that can be propagated.

One disadvantage observed with current cDNA library synthesis protocols is that current methods tend to produce libraries having a significant proportion of incomplete cDNAs, which results from inefficiencies in the reverse transcriptase employed to generate the library. To compensate for the incomplete cDNA constituents of the library, investigators must perform many rounds of isolation (screenings) and construct a "full-length" cDNA from the accumulated pieces. Such processes are resource intensive and do not ensure that each initial mRNA is represented in the cDNA library.

In addition, there is significant under-representation of sequences close to the 5' end of mRNAs since in cDNA libraries produced by convention methods. This under-representation results from the fact that the reverse transcriptase will usually "fall off" before reaching these sequences.

Another problem concerning cDNA synthesis is the source and quality of the mRNA used. Using present day technology, the mRNA that is used as a source for cDNA synthesis is purified by its 3' end polyadenylated tail. However, some mRNAs do not possess a 3' end but all mRNAs have a 5' cap structure. Consequently, a cDNA library constructed from this source of mRNA would be more representative of the total genetic information present in the cell. In recent years, unsuccessful attempts have been made to develop antibodies directed against the cap structure of mRNA. The problems usually encountered were related to the insufficient affinity of the antibodies for the cap. This major drawback made it impossible to develop isolation protocols for capped mRNAs.

Therefore, there is continued interest in the development of new methods of cDNA synthesis.

Relevant Literature

U.S. patents of interest include U.S. Pat. No. 5,219,989. Strategies for producing full length cDNAs are described in: Edery, et al., "An efficient strategy to isolate full-length cDNAs based on an mRNA cap retention procedure (CAPture)," Mol Cell Biol (June, 1995)15(6):3363–71; Suzuki et al., "Construction and characterization of a full length-enriched and a 5'-end-enriched cDNA library," Gene (Oct. 24, 1997) 200(1–2):149–56; Alphey, "PCR-based method for isolation of full-length clones and splice variants from cDNA libraries," Biotechniques (March 1997)22(3):481–4, 486; Carninci et al., "High efficiency selection of full-length cDNA by improved biotinylated cap trapper," DNA Res (Feb. 28, 1997) 4(1):61–6; Carninci et al., "High-efficiency full-length cDNA cloning by biotinylated CAP trapper," Genomics (Nov. 1, 1996)37(3):327–36; Schmid et al., "A procedure for selective full length cDNA cloning of specific RNA species," Nucleic Acids Res (May 26, 1987) 15(10):3987–96; Seki et al., "High-efficiency cloning of Arabidopsis full-length cDNA by biotinylated CAP trapper," Plant J (September 1998) 15(5):707–20; Okayama et al., "High-efficiency cloning of full-length cDNA," Mol Cell Biol (February 1982) 2(2):161–70; Sekine et al., "Synthesis of full-length cDNA using DNA-capped mRNA," Nucleic Acids Symp Ser (1993) (29):143–4.

eIF-4E is described in Altmann et al., "mRNA cap-binding protein: cloning of the gene encoding protein synthesis initiation factor eIF-4E from *Saccharomyces cerevisiae*," Mol Cell Biol (March 1987) 7(3):998–1003. eIF-4G is described in Hentze, Science (Jan. 24, 1997) 275: 500 and Haghighat et al., J. Biol. Chem. (Aug. 29, 1997) 272:21677.

SUMMARY OF THE INVENTION

Methods and compositions are provided for producing full-length cDNA libraries. In the subject methods, full length first strand cDNAs are isolated using a fusion protein of an eIF-4E domain and an eIF-4G domain separated by a flexible linker. Also provided is the novel fusion protein employed in the subject methods, as well as nucleic acids encoding, and host cells capable of expressing, the same. Finally, kits for use in practicing the subject methods are provided. The subject invention finds use in a variety of applications in which full-length cDNA libraries are employed.

DESCRIPTION OF THE SPECIFIC EMBODIMENTS

Figure 1:
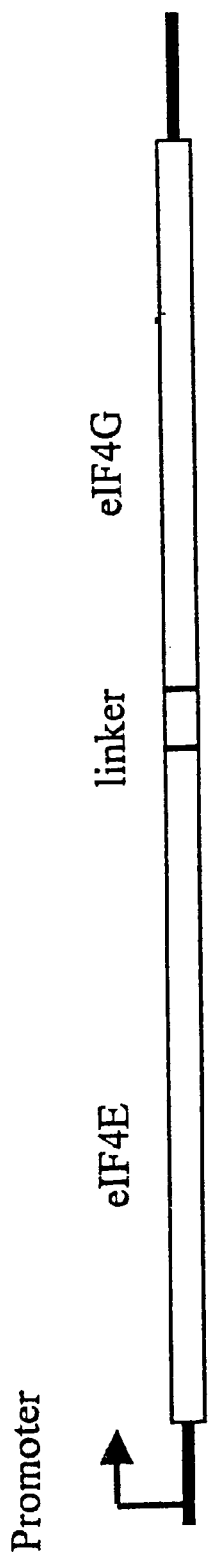
FIG. 1 provides schematic of the expression construct encoding a fusion protein according to the subject invention.
Figure 2:
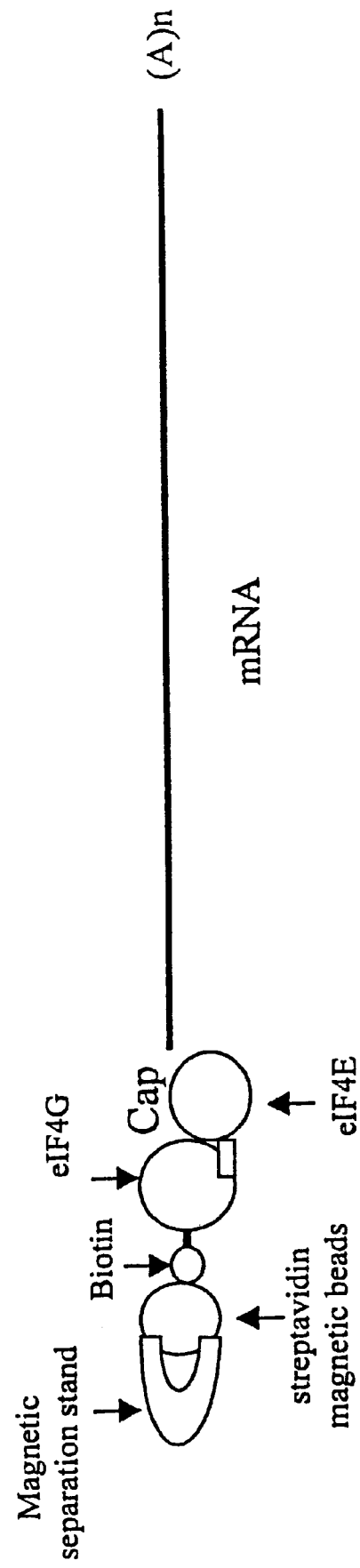
FIG. 2 provides a representation a complex of the subject fusion protein with mRNA bound to a solid support.
Figure 3:
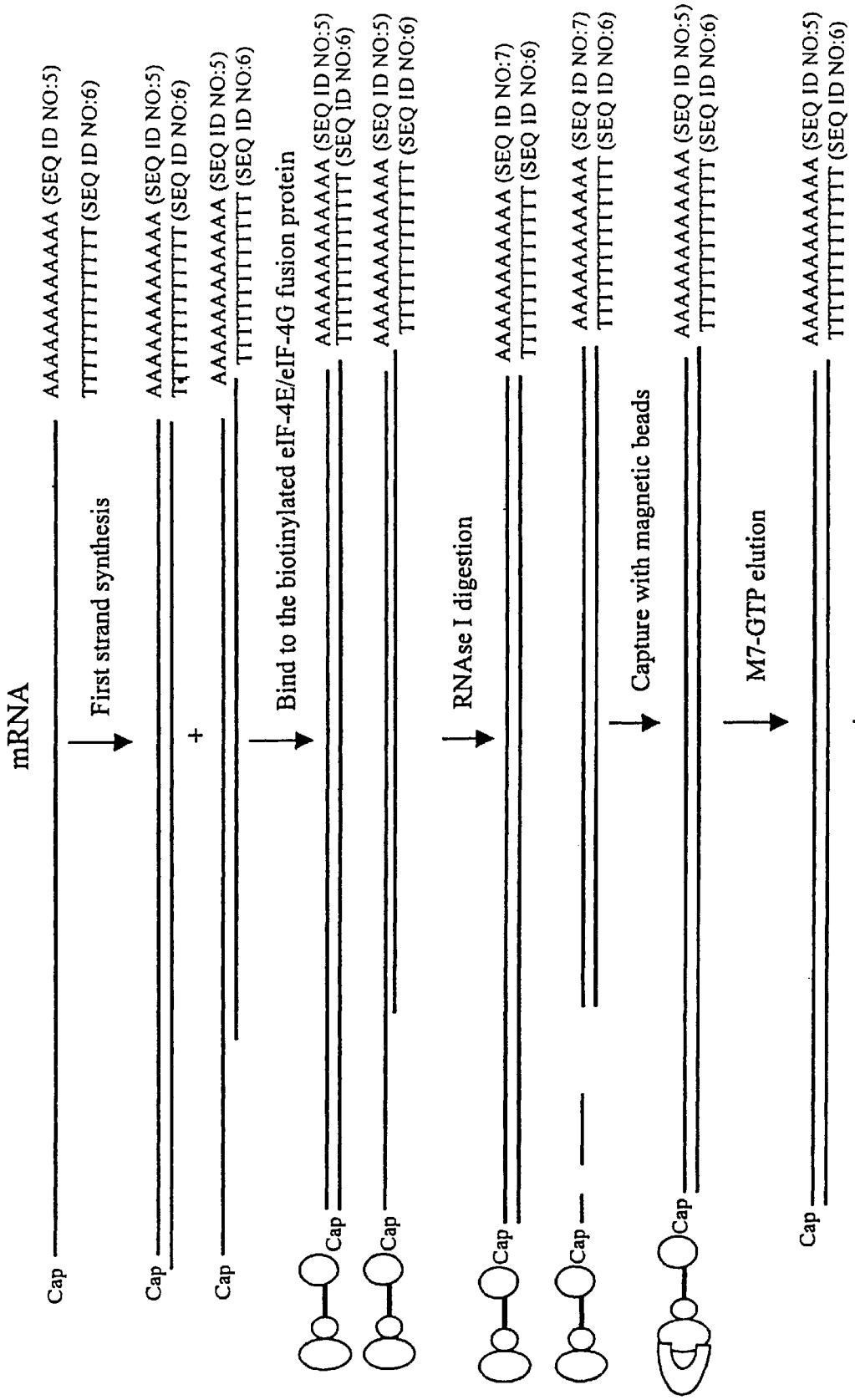
FIG. 3 provides a schematic of the preparation cDNA library according to the subject invention.

Methods and compositions are provided for producing full-length cDNA libraries. In the subject methods, full length first strand cDNAs are isolated using a fusion protein of an eIF-4E domain and an eIF-4G domain separated by a flexible linker. Also provided is the novel fusion protein employed in the subject methods, as well as nucleic acids encoding, and host cells capable of expressing, the same. Finally, kits for use in practicing the subject methods are provided. The subject invention finds use in a variety of applications in which full-length cDNA libraries are employed. In further describing the subject invention, the subject methods will be discussed first, followed by a description of the kits of the invention.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

In the broadest sense, the subject invention is a method of isolating a nucleic acid having a 5' cap structure. Any nucleic acid may be isolated through use of the subject methods, as long as the nucleic acid has a 5' cap structure. By 5' cap structure is meant the 5' structure found on eukaryotic mRNAs, i.e. 5' terminal m7 GpppN (where N is any nucleotide). See Banerjee, Microbiol. Rev. (1980) 44: 175–205 and Shatkin, Cell (1985) 40:223–224 for further description of the 5' cap structure. The nucleic acids may be naturally produced or synthetic nucleic acids, and may be single stranded or double stranded. The subject methods are particularly suited for use in the isolation of single-stranded mRNA or double-stranded mRNA:cDNA duplexes or hybrid complexes.

A critical aspect of the subject invention is the use of an eIF-4E/eIF-4G fusion protein. The subject eIF-4E/eIF-4G fusion protein has at least the following features: an eIF-4E domain, and eIF-4G domain; and a linker domain that joins the eIF-4E and eIF-4G domains with a flexible linkage. The eIF-4E domain may be derived from any convenient eukaryotic source, e.g. animal, plant, yeast, etc., and may include the amino acid sequence of an entire eIF-4E protein or a fragment thereof, e.g. an eIF-4E fragment that exhibits the requisite 5' cap structure binding activity. A number of eIF-4E proteins from different eucaryotes are known, including rabbit, mouse, human, yeast etc., where the eIF-4E domain in the subject fusion protein may be one of these or a derivative (including mutant) thereof, as long as the requisite 5' cap structure binding activity is retained. Generally, the length of this domain ranges from about 100 to 200, usually from about 125 to 175 and more usually from about 150 to 175 aa.

As with the eIF-4E domain, the eIF-4G domain may be derived from any convenient eukaryotic source, such as animal, plant, yeast, insect and the like, such as human, mouse, rabbit, fruit fly, wheat germ etc. The eIF-4G domain may include the amino acid sequence of an entire eIF-4G protein or a fragment thereof, e.g. an eIF-4G fragment that exhibits the requisite ability to enhance the 5' cap structure binding activity of eIF-4E, as well as a derivative or mutant thereof. The length of this domain typically ranges from about 100 to 500, usually from about 100 to 300 and more usually from about 150 to 200 aa long, where a domain that incorporates residues 318 to 478 of the wild type eIF-4G or the equivalent thereof is of particular interest in many embodiments.

Joining the eIF-4E and eIF-4G domains is the linker domain. The linker domain is a flexible linker that is of sufficient length to provide for substantially free movement of the two eIF domains relative to each other. Because of the manner in which the fusion protein is produced, the linker domain is generally, though not necessarily, a stretch of amino acids, where the stretch of amino acids is generally at least about 5 aa in length, usually at least about 10 aa in length and more usually at least about 20 aa in length, where the linker may be 100 aa in length or longer, but generally will not exceed about 100 aa in length and usually will not exceed about 50 aa in length. The amino acid sequence of the linking domain may be any convenient sequence, as long as the sequence does not give rise to some stable secondary structure that may diminish the flexibility of the domain, e.g. an α-helical structure. Of interest in many embodiments are linking sequences derived from RNA binding proteins, e.g. hnRNAPA.

In addition to the above domains, the eIF-4E/eIF-4G fusion protein also generally includes an additional domain for stably associating the fusion protein to a solid support. In the broadest sense, this additional domain may provide for any type of stable association with a solid support, including covalent or non-covalent association. However, in many preferred embodiments, this additional domain provides for non-covalent, stable association with a solid support. By stable association is meant that the domain, and therefore the fusion protein of which the domain is part, remains bound to the solid support under a given set of conditions, e.g. a pH ranging from about 6.0 to 8.0, usually from about 7.0 to 7.5; a salt concentration ranging from about 0 to 1.0 M, usually from about 0.1 to 0.2 M; and a temperature ranging from about 0 to 22° C., usually from about 0 to 4° C. Typically, this domain of the subject fusion proteins is a member of a specific binding pair, where specific binding pairs of interest include: ligands/receptors; antigens/antibodies or binding fragments thereof, and the like. Specific solid support binding domains of interest include: protein A, the FLAG epitope, biotin, His tag, and the like.

The subject fusion proteins are further characterized in that they have a significantly enhanced 5' cap recognition activity as compared to eIF-4E by itself. By significantly enhanced is meant that cap recognition activity is at least 5 fold, usually at least about 20 fold and more usually at least about 200 fold greater than that observed in eIF-4E by itself, as measure by electrophoretic mobility shift (see Experimental Section).

The molecular weight of the subject fusion proteins may vary somewhat depending on the nature of the linker domain and the solid phase binding domain, if present. However, the molecular weight of the subject proteins ranges from about 20 kD to 60 kD, usually from about 40 kD to 55 kD and more usually from about 40 to 50 kD, where in many embodiments the molecular weight is about 45 kD.

The subject fusion protein may be made using any convenient protocol, where protocols for preparing fusion proteins are well known to those of skill in the art. In general, a vector is constructed using restriction endonucleases, ligase etc., which comprises an expression construct having a nucleic acid that encodes the subject fusion protein, e.g. a nucleic acid that includes coding sequence for the fusion protein, e.g. the solid support binding domain, the eIF-4E domain, the eIF-4G domain, the flexible linker, etc. A representative expression construct is depicted in FIG. 1. The vector is then used to transform as suitable expression host, e.g. *E.coli*, which host is then cultured to produce the fusion protein, which is ultimately harvested and isolated. A representative protocol which may be modified (e.g. by introducing a gene encoding the eIF-4G domain) to produce the fusion proteins of the present invention can be found U.S. Pat. No. 5,219,989, the disclosure of which is herein incorporated by reference.

Turning now to the subject methods, common features to all of the embodiments of the subject invention are: (1) contacting a nucleic acid having a 5' cap structure with a fusion protein according to the subject invention under conditions sufficient to form a complex between said nucleic acid and said fusion protein; and (2) isolating the resultant complex.

As summarized above, the first common step in all of the embodiments of the subject invention is to contact the fusion protein with the nucleic acid. The nucleic acid is typically an mRNA or an mRNA derivative, e.g. a cDNA/mRNA duplex. The initial mRNA may be present in a variety of different samples, where the sample will typically be derived from a physiological source. The physiological source may be derived from a variety of eukaryotic sources, with physiological sources of interest including sources derived from single celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNAs to be analyzed from the physiological source from which it is derived, the physiological source may be subjected to a number of different processing steps, where such processing steps might include tissue homogenation, cell isolation and cytoplasmic extraction, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press)(1989).

Contact is brought about using any convenient protocol, such as introducing a quantity of fusion protein into an aqueous medium comprising the nucleic acids of interest or vice versa. Contact occurs under conditions sufficient for the fusion protein to stably bind to the 5' cap structure of the nucleic acid. Generally, contact occurs in an aqueous media ranging in pH from about 6.5 to 8.5, usually from about 7.0 to 8.0. In addition to the fusion protein and the nucleic acid, the aqueous media may include one or more buffering agents, ions, chelators, antioxidants, glycerol, tRNA and the like. In contacting the fusion protein with the nucleic acid, the fusion protein is generally incubated with the nucleic acid for a sufficient period time and at a sufficient temperature for substantially all potential complexes between the fusion proteins and nucleic acids present in the aqueous mixture to occur. Incubation generally lasts for a period of time ranging from about 5 to 30 min, usually from about 10 to 25 min and more usually from about 15 to 20 min. The temperature at which incubation is carried out typically ranges from about 0 to 22° C., usually from about 0 to 4° C.

Depending on the particular embodiment being performed, the fusion protein may or may not be stably associated with a solid support prior to contact with the nucleic acids. Thus, in one embodiment, the fusion protein is pre-bound to a solid support prior to contact with the nucleic acids. In another embodiment, the fusion protein is not bound to a solid support prior to contact with the nucleic acids. In this latter embodiment, following complex formation, a solid support may be introduced into the aqueous mixture under conditions sufficient for the solid support to bind to the fusion protein moiety of the complex. The solid support may be any convenient solid support. Generally the solid support or solid phase has a member of a specific binding pair on its surface which is capable of specifically binding to a moiety present on the fusion protein/nucleic acid complexes of the subject invention. A variety of different solid-phases are suitable for use in the subject methods, such phases being known in the art and commercially available. Specific solid phases of interest include polymeric, e.g. polystyrene, pegs, sheets, beads, magnetic beads, and the like. The surfaces of such solid phases have been modified to comprise the specific binding pair member, e.g. for biotinylated primer extension products, streptavidin coated magnetic bead may be employed as the solid phase. In yet other embodiments, e.g. where a solid support is not critical to the isolation of the fusion protein nucleic acid complex, the fusion protein is not pre-bound to a solid support and is not bound to a solid support at any time in the process.

Following formation of the fusion protein and nucleic acid complexes, as well as stable association of the complexes to solid supports (when desired), the resultant complexes are isolated. By isolated is meant that the complexes are at least separated from at least some of the remaining components of the reaction mixture in which they are present following complex formation. For example, "separating" as used herein includes removing a portion of the water from the reaction mixture that includes the complexes, such that the complexes are concentrated. Separating also includes retrieving the complexes from the remainder of the reaction mixture constituents. Any convenient isolation protocol may be employed, where the particular protocol chosen generally depends on the nature of the complexes that are being isolated. For example, in those preferred embodiments in which the complexes are stably associated via the fusion protein to a solid support, separation or isolation typically involves concentration of the solid supports, e.g. by centrifugation, etc.

In certain embodiments of the subject invention, e.g. in the preparation of a cDNA library, the above methods are modified through the addition of the following steps: (1) a first strand cDNA synthesis step; and (b) an RNAse treatment step; which two steps are performed prior to the complex isolation step.

First strand cDNA synthesis is performed using any convenient protocol. In preparing the first strand cDNA, a primer is contacted with the mRNA with a reverse transcriptase and other reagents necessary for primer extension under conditions sufficient for first strand cDNA synthesis to occur. Although both random and specific primers may be employed, in many embodiments the primer is an oligo dT primer that provides for hybridization to a polyA tail of an mRNA. The oligo dT primer will be sufficiently long to provide for efficient hybridization to the polyA tail, where the primer will typically range in length from 10 to 25 nt in length, usually 10 to 20 nt in length, and more usually from 12 to 18 nt length. Additional reagents that may be present include: dNTPs; buffering agents, e.g. Tris-Cl; cationic sources, both monovalent and divalent, e.g. KCl, $MgCl_2$; sulfhydril reagents, e.g. dithiothreitol; and the like. A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776 (the disclosures of which patents are herein incorporated by reference), human T-cell leukemia virus type I (HTLV-I), bovine leukemia virus (BLV), Rous sarcoma virus (RSV), human immunodeficiency virus (HIV) and *Thermus aquaticus* (Taq) or *Thermus thermophilus* (Tth) as described in U.S. Pat. No. 5,322,770, the disclosure of which is herein incorporated by reference, avian reverse transcriptase, and the like. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like. Of particular interest because of their commercial availability and well characterized properties are avian reverse transcriptase and M-MLV.

The order in which the reagents are combined may be modified as desired. One protocol that may be used involves the combination of all reagents except for the reverse transcriptase on ice, then adding the reverse transcriptase and mixing at around 4° C. Following mixing, the temperature of the reaction mixture is raised to 37° C. followed by incubation for a period of time sufficient for first strand cDNA primer extension product to form, usually about 1 hour.

Following first strand cDNA synthesis, the resultant duplex mRNA/cDNA (i.e. hybrid) is then contacted with an RNAse capable of degrading single stranded RNA but not RNA complexed to DNA under conditions sufficient for any single stranded RNA to be degraded. A variety of different RNAses may be employed, where known suitable RNAses include: RNAse T1 from *Aspergillus orzyae*, RNase I, RNase A and the like. The exact conditions and duration of incubation during this step will vary depending on the specific nuclease employed. However, the temperature is generally between about 20 to 37° C., and usually between about 25 to 37° C. Incubation usually lasts for a period of time ranging from about 10 to 60 min, usually from about 15 to 60 min.

Nuclease treatment results in the production of blunt-ended mRNA/cDNA duplexes or hybrids. In the resultant mixture, those mRNA/cDNA hybrids that include a full length cDNA will have the 5' cap structure of the template mRNA, while those in which a full length cDNA was not produced in the reverse transcription step will not. Following production of the blunt-ended mRNA/cDNA hybrids, the resultant hybrids are then contacted with the fusion protein and isolated as described above.

Following isolation, the nucleic acids may be further processed as desired, where further processing includes: release from the solid phase support (if present), e.g. by cleavage reaction, disruption of the specific bond, and the like; production of double stranded cDNA, etc., where protocols for performing such operations are well known to those of skill in the art.

The subject methods find use in a variety of applications in which isolation of full length mRNA and/or cDNAs is desired. Such applications include: mRNA isolation, cDNA library construction, and the like. For example, where one desires to construct a cDNA library, mRNA/cDNA hybrids comprising full length cDNAs from the initial sample can be prepared as described above. The resultant hybrids are then converted to double stranded cDNAs which are then inserted to a vector, e.g. plasmid, phage, etc., for subsequent propagation and use.

Also provided by the subject invention are kits for carrying out the subject methods. The kits of the subject invention include at least the fusion protein of the subject invention, i.e. a fusion protein that includes at least an eIF-4E domain, a linker domain and an eIF-4G domain. The kit may further include a solid phase, such as those described above, and one or more reagents for carrying the claimed methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, T1 RNAse, primers (e.g., appropriate length poly(T) or random primers), and the like. A set of instructions will also typically be included, where the instructions may be associated with a package insert and/or the packaging of the kit or the components thereof.

The following examples are offered by way of illustration and not by way of limitation.

Experimental

I. Methods and Compositions for Producing Full Length cDNA Libraries

A. Construction of Expressible eIF-4E/eIF-4G Fusion Protein

Amplification of DNA Sequences from cDNA Library (1) Prepare PCR reaction cocktail:

1.5 mM $MgCl_2$ 16.6 mM $NH_4SO_4$ 2.8 mM β-mercaptoethanol 0.68 μM EDTA, pH 8.0

67 mM Tris-HCl (pH 8.8)

0.1% Tween™-20

0.2 mM dNTP (each)

0.03 units/μL Taq Polymerase (5units/μL)

0.00178 units/μL Pfu 2.5 units/μL (2) Dilute 5' & 3' primer pairs to 50 μM each in 1.5 mL tube for eIF-4E and eIF-4G individually.

(3) Transfer 100 μL of PCR cocktail to 2 reaction tubes on ice.

(4) Add 1 μL of eIF-4E and eIF-4G primer pairs to individual reaction tubes. The final concentration of each primer is 0.5 μM.

(5) Add 1 μL of cDNA Human Liver Library to each reaction.

(6) Cycle:

1) 94° C. for 3 minutes
2) 94° C. for 15 seconds
3) 0.5° C./sec to 50° C.
4) 50° C. for 1 minute
5) 72° C. for 4 minutes
6) Go to step 2, 34×
7) 72° C. for 8 minutes
8) 4° C. Forever
9) End (7) Prepare 0.8% SeaKem GTG Agarose [FMC Cat. No. 50074] gel+EtBr and load 50 μL of PCR reactions. Run gel 360 v-hr.

(8) Remove gel slices and extract PCR products using QIAquick Gel Extraction Kit [QIAGEN Cat. No. 28704]. Resuspend purified products in 30 μL EB buffer.

Restriction Digest of PCR Products & pET-15b Expression Vector

| | | |
|---|---|---|
| (1) eIF-4E Digestion | 25 μL | Purified PCR Product |
| | 5 μL | 10X NE Buffer 4 |
| | 18 μL | RNase free H$_2$O |
| | 1 μL | Nco I (10 units/μL) |
| | 1 μL | Ban I (20 units/μL) |
| | Incubate @ 37° C., 4.25 hours | |
| (2) eIF-4G Digestion | 25 μL | Purified PCR Product |
| | 5 μL | 10X NE Buffer 2 |
| | 0.5 μL | 100X BSA |
| | 17.5 μL | RNase free H2O |
| | 1 μL | Ban I (20 units/μL) |
| | 1 μL | Xho I (20 units/μL) |
| | Incubate @ 37° C., 4.25 hours | |
| (3) pET-15b Vector [Novagen Cat. No. 69661-3] | 8.1 μL | 0.37 μg/μL pET-15b Vector |
| | 5 μL | 10X NE Buffer 2 |
| | 5 μL | 10X BSA |
| | 29.9 μL | RNase Free H2O |
| | 1 μL | Nco I (10 units/μL) |
| | 1 μL | Xho I (20 units/μL) |
| | Incubate @ 37° C., 2.0 hours | |

(4) Prepare 0.8% SeaKem GTG Agarose gel+EtBr and load 50 μL of RE digestion reactions. Run gel 200 v-hr.

(5) Remove gel slices and extract using QIAquick Gel Extraction Kit. Resuspend purified products in 30 μL EB buffer.

(6) Prepare 0.8% SeaKem LE Agarose [FMC Cat. No. 50004] gel+EtBr and load 5 μL of RE digested PCR products to estimate concentration.

eIF-4E/eIF-4G Construct Ligation
Prepare ligation reaction at 1:1:1 (Vector:eIF-4E:eIF-4G)
X μL pET-15b NcoI/XhoI
X μL eIF-4E NcoI/BanI
X μL eIF-4G BanI/XhoI
2 μL 10×T4 DNA Ligase Buffer
X μL DI H$_2$O
1 μL T4 DNA Ligase (400 units/μL)
20 μL, Incubate @ 16° C. overnight (16 hours).

B. Expression & Purification of eIF-4E/eIF-4G Fusion Protein

Transformation to DH10B Cells
Transfer 1 μL of ligation to 1.5 mL μfuge tube on ice.

Add 50 μL ElectroMAX DH10B Cells [Gibco-BRL Cat. No. 18290-015]. Mix gently.
Transfer DNA/Cells to 0.1 cm gap cuvette on ice.
Electroporate @ 2.5 kv.
Recover cells in 1 mL SOC (pH 7.0, 22° C.). Incubate @ 37° C., 60 minutes, 250 rpm.
Plate 10 μL & 100 μL of transformation on LB+2× Carbenicillin (100 μg/mL).
Incubate 37° C. overnight (16 hours).

Plasmid Preparation
Inoculate 25 mL LB+2×Carbenicillin (100 μg/mL) with individual colony.

Incubate @ 37° C., 250 rpm, overnight (16 hours).
Purify plasmid using QIAgen Plasmid Midi Kit [QIAGEN Cat. No. 12143].

Resuspend DNA in 100 μL 10 mM Tris-HCL pH 7.5.
Sequencing of the construct is recommended to confirm the sequence of the construct.

Transformation of eIF-4E/eIF-4G Fusion Protein Construct to BL21(DE3)pLysS Cells
(1) Dilute purified plasmid to 1 ng/μL.

Transfer 1 μL of plasmid to 1.5 mL μfuge tube on ice.
Add 20 μL BL21(DE3)pLysS cells [Novagen Cat. No. 69451-4] to tube and mix gently.
Incubate on ice 30 minutes.
Heat shock DNA/Cells @ 42° C. for 40 seconds. Transfer to ice for 2 minutes.
Add 180 μL SOC (pH 7.0, 22° C.) and transfer entire volume to Falcon 2059 tube.
Incubate 37° C., 200–250 rpm, 60 minutes.
Plate 10 μL & 100 μL of transformation on LB+2× Carbenicillin (100 μg/mL)+Chloramphenicol (34 μg/mL).
Incubate 37° C. overnight (16 hours).

C. Purification of Expressed eIF-4E/eIF-4G Fusion Protein
Day 1
Inoculate 100 mL of LB+2×Carbenicillin (100 μg/mL)+Chloramphenicol (34 μg/mL) with single colony from transformation plates.

Incubate 37° C., 250 rpm, overnight (16 hours).

Day 2
Inoculate 8×500 mL LB+2×Carbenicillin (100 μg/mL)+Chloramphenicol (34 μg/mL) with 1 mL of overnight culture.

Incubate 37° C., 225 rpm, OD$_{600}$=0.6.
Add 5 mL 100 mM ITPG (C$_f$=1 mM). Incubate 37° C., 225 rpm, 2 hours.

All Following Steps Performed at 4° C.
Split each 500 mL culture into 2×250 mL volumes and pellet cells @ 2000×g, 15 min, 4° C.

Carefully remove supernatants. Resuspend both pellets in single 20 mL volume of Sonication Buffer [20 mM HEPES (pH 7.5), 0.5 M KCL, 0.2 mM EDTA, 0.5% NP-40].
Transfer 20 mL volume (per 500 mL culture) to Falcon 35-2070, 50 mL polypropylene tubes on ice.
Prepare Sonicator Ultrasonic Processor XL, Misonix Inc. by filling cup horn with 4° C. H$_2$O.
Sonicate cells for 2×60 seconds pulses @ power level 7.
Transfer sonicated cell suspensions to 40 mL Oakridge tubes and centrifuge @ 10,000×g for 15 minutes.
Pool all supernatants into 1 liter polypropylene flask and dilute 5 fold with Dilution Buffer [20 mM HEPES (pH 7.5), 0.2 mM EDTA, 1 mM Dithiothreitol, 10% Glycerol] to decrease [KCl] to 0.1M. Store on ice @ 4° C.

Column Chromatography Preparation
Pool 4×1 mL 7-methylguanosine 5'-triphosphate (m7-GTP) immobilized on Sepharose 4B [Sigma cat. no. M-4648] to Falcon 2059 tube. Rinse vials with Wash Buffer [20 mM HEPES (pH 7.5), 100 mM KCl, 0.2 mM EDTA, 1 mM Dithiothreitol, 10% Glycerol] to collect all sepharose beads.

Rinse 10 mL Column (BioRad) with 20 mL DI H$_2$O. Add 3 mL Wash Buffer to the column and cap.

Load the m7-GTP sepharose beads into the column under the control of a peristaltic pump.
Wash beads with 20 mL Wash Buffer (5 volumes) and 80 mL Sonication Buffer (20 volumes).
Equilibrate column with 40 mL Wash Buffer (10 volumes).

Column Loading/Purification
Load protein suspension to column @ 75 mL/hour using peristaltic pump.

Wash column with 200 mL Wash Buffer @ 75 mL/hour using peristaltic pump.
Prepare 500 μM 7-methylguanosine 5'-triphosphate (m7-GTP) [Sigma Cat. No. M-6133] in 10 μL Wash Buffer.
Drain column until the meniscus is just above the column bead. Carefully add 4 mL of 500 μM m7-GTP and allow column to flow until the elution buffer has completely entered the beads. Stop flow and let stand 20 minutes.
Add 4 mL of Wash Buffer and collect 4 mL of eluted protein in 14 mL Falcon 2059 tubes.

SDS-PAGE Analysis of Purified eIF-4E/eIF-4G Fusion Protein

Prepare SDS-PAGE gel:

| Reagent | 5% Stacking Gel | 12% Resolving Gel |
|---|---|---|
| 40% Acrylamide | 2.5 mL | 15 mL |
| 1M Tris-HCl | 2.5 mL (pH 6.8) | 12.5 mL (pH 8.8) |
| 20% SDS | 0.1 mL | 0.25 mL |
| 10% Ammonium Persulfate | 0.1 mL | 0.5 mL |
| TEMED | 0.02 mL | 0.05 mL |
| DI H$_2$O | to 20 mL | to 50 mL |

Pour gel and let polymerize.

(1) Prerun gel for 20 minutes @ 200 volts in 1×Tris/Glycine/SDS Buffer [Prepared from 10×Tris/Glycine/SDS Buffer, BioRad Cat. No. 161-0732].

(2) Protein sample preparation: Dilute 100 μL of purified 4E/4G Fusion protein 1:1 with SDS Reducing Sample Buffer [Laemmli Sample Buffer BioRad Cat. No. 161-0737]. Heat sample 70° C. for 5 minutes.

(3) Prepare SDS-Broad Range Standards [BioRad Cat. No. 161-0317]. Heat 70° C. for 5 minutes.

(4) Load 10 μL SDS-Broad Range Standard and 200 μL protein sample to gel.

Run gel 450 volt-hours.
Stain gel using 1×Coomassie Stain Solution [BioRad Cat. No. 161-0436].
Destain gel using 1×Destain Solution, Coomassie R-250 [BioRad Cat. No. 161-0438].
Expected protein size is approx. 46 kDa.
Load protein to Pierce Slide-A-Lyzer 2,000 MWCO dialysis cassette [Pierce Cat. No. 66210]. Dialyze against 2×1500 mL Wash Buffer and 2×1500 mL 2×Storage Buffer [40 mM HEPES-KOH (pH 7.5), 0.2 mM EDTA, 2 mM DTT, 200 mM KCl].
Remove protein sample from cassette and store at 4° C.
Quantitate protein using Coomassie Plus-200 Protein Assay Reagent [Pierce 23238].

D. Mobility Shift Assay
Produce $^{32}$P-labelled capped and uncapped run off RNA using TransProbe T [Pharmacia Biotech 27-9276-01] to test the binding affinity of the fusion protein. Purify capped run off RNA from Native-PAGE gel. Store @ −80° C. in RNase free H$_2$O. Gel preparation: 6% polyacrylamide native gel

| Reagent | Volume |
|---|---|
| 40% Acrylamide | 7.5 mL |
| 10 × TBE | 5.0 mL |
| 10% Ammonium Persulfate | 0.5 mL |
| TEMED | 1.0 mL |
| DI H2O | to 50 mL |

Pour gel using 20 well comb. Allow to polymerize and chill to @ 4° C.
Prepare 4×Binding Buffer:
40 mM HEPES-KOH, pH 7.5
400 MM KCl
4 mM MgCl$_2$
2.0 mM EDTA
4 mM DTT
40% Glycerol
Dilute 4E/4G fusion protein to 16 μL/sample in Wash Buffer.
Create protein range from 5 ng–250 ng in 1.5 mL μfuge tubes on ice.

Prepare RNA (capped & uncapped) cocktails at 16 μL/sample in 2×Binding Buffer.
Mix protein with capped and uncapped RNA samples and incubate 15 minutes [Binding Buffer becomes 1×on ice.
Run gel 600 v-hr in 1×TBE @ 4° C. Dry gel for 30 minutes at 80° C.
Autoradiograph with an intensifying screen at −80° C.
Compare binding affinity between capped and uncapped RNA. The 4E/4G fusion protein binds the capped RNA at the 5–10 nM range. Non-specific binding at the 70–140 nM range occurs with the uncapped RNA.
E. Biotinylation of eIF-4E/eIF-4G Fusion Protein
Concentrate protein to 1.5–2.0 mg/mL using Millipore Microcon 10,000 MWCO microconcentrator [Millipore Cat. No. 42422]

Follow protocol supplied with EZ-Link NHS-LC-LC-Biotin [Pierce Cat. No. 21343].
Quantitate biotinylation using ImmunoPure HABA [Pierce Cat. No. 28050].
Quantitate protein concentration post-biotinylation using Coomassie Plus-200 Protein Assay Reagent [Pierce 23238].
Verify the binding affinity post-biotinylation using Mobility Shift assay explained above. The 4E/4G fusion protein binds the capped RNA at a range of 3.5–7.0 nM after biotinylation.

F. Coupling of 4E/4G Fusion Protein to StreptAvidin Beads
Remove 100 μL Dynabeads M-280 StreptAvidin [Dynal Cat. No. 112.06] per μg protein and transfer to 1.5 mL μfuge tube.

Remove supernatant by magnetic separation and wash beads 3×w/100 μL of 2×Storage Buffer.
Dilute 4E/4G Fusion protein (1 μg/50 μL) in 2×Storage Buffer.
Resuspend beads in 50 μL diluted protein after final wash with 2×Storage Buffer.
Incubate @ 4° C. for 30 minutes. Mix by gentle pipeting every 5 minutes. Remove supernatant by magnetic separation and wash 3×w/50 μL 1×Binding Buffer [10 mM HEPES-KOH (pH 7.5), 100 mM KCl, 1 mM MgCl$_2$, 0.5 mM EDTA, 1 mM Dithiothreitol, 10% Glycerol]. Store @ 4° C.

G. Synthesis of mRNA/DNA Hybrid

[Reagents used from SUPERSCRIPT Plasmid System for cDNA Synthesis and plasmid Cloning]

(1) Annealing, add a mixture of 2.5 μL mRNA polyA$^+$ (1 μg/μL), 2 μL oligo dT Not I primer adapter, and 5.5 μL of RNase free H$_2$O.

(2) 70° C., 10 minutes, chill on ice for 5 minutes, spin to collect and suspend.

(3) First Strand reaction with oligo-dT

| Add iced cocktail containing | 4 μL 5 × 1st Strand Buffer |
|---|---|
| | 2 μL 0.1 M DTT |
| | 1 μL 10 mM dNTPs |
| | 1 μL [α-32P]dCTP (10 μci/μl) 37° C. | for 2 minutes to equilibrate the temperature. Add 2 μL SuperScript II RT. Total 20 μL, mix, incubate at 37° C. for 60 minutes.

Add equal volume of Phenol:Choloroform:Isoamyl alcohol (25:24:1). Vortex thoroughly and centrifuge 14,000×g at room temperature for 5 minutes. Carefully remove the upper aqueous layer and transfer to a new tube.

Add ½ volume (10 μL) 7.5M NH4OAC, 3 volumes (−20° C.) 100% ethanol (90 μl), mix, centrifuge at 20,000×g, 4° C., 20 minutes. Carefully remove the supernatant.

The pellet is washed with 200 μL of 70% ethanol (−20° C.) and centrifuged at 20,000×g for 5 minutes. Remove supernatant carefully and dry.

H. RNase One Treatment of mRNA/DNA Hybrid

Resuspend mRNA/DNA hybrid in 40 μL RNase free H$_2$O.

Add 5 μL 10×RNase One Buffer and 5 μL RNase One (10 units/μL) [Promega Cat. No. M4261].

Incubate @ 37° C., 15 minutes.

Add equal volume of Phenol:Choloroform:Isoamyl alcohol (25:24:1). Vortex thoroughly and centrifuge 14,000×g at room temperature for 5 minutes. Carefully remove the upper aqueous layer and transfer to a new tube.

Add ½ volume (25 μL) 7.5M NH$_4$OAC, 3 volumes (−20° C.) 100% ethanol (225 μL), mix, centrifuge at 20,000×g, 4° C., 20 minutes. Carefully remove the supernatant.

The pellet is washed with 500 μL of 70% ethanol (−20° C.) and centrifuged at 20,000×g for 5 minutes. Remove supernatant carefully and dry.

I. Capture of mRNA/DNA Hybrid Using eIF-4E/eIF-4G Fusion Protein (1) Resuspend RNase One treated mRNA/DNA hybrid in 50 μL of 1×Binding Buffer.

(2) After final wash with 1×Binding Buffer, resuspend protein beads in 50 μL of diluted mRNA.

(3) Incubate on ice (4° C. BioCold) for 15 minutes. Mix by gentle pipeting every 5 minutes.

(4) Remove the supernatant by magnetic separation and wash 5×w/50 μL 1×Binding Buffer+0.3M KCl+0.1% NP-40. Collect all wash volumes in 1.5 mL μfuge tube for counting.

Elute mRNA from protein beads by resuspending in 50 μL 1×Binding Buffer+0.3M KCl+0.1% NP-40+1 mM M7-GTP.

Incubate @ 4° C. for 5–15 minutes. Mix by gentle pipet every 5 minutes if incubating for periods greater than 5 minutes. Remove the supernatant by magnetic separation and repeat elution step. Pool elution volumes (100 μL).

Add ½ volume (50 μL) 7.5M NH$_4$OAC, 3 volumes (−20° C.) 100% ethanol (450 μL), mix, centrifuge at 20,000×g, 4° C., 20 minutes. Carefully remove the supernatant.

The pellet is washed with 500 μL of 70% ethanol (−20° C.) and centrifuged at 20,000×g for 5 minutes. Remove supernatant carefully and dry.

J. Completion of FL-cDNA Library [2nd Strand Synthesis]

Resuspend captured RNA/DNA hybrid in 13 μL RNase free H$_2$O.

On ice add cocktail containing

Recreate 1$^{st}$ Strand conditions by adding

4 μL 5×1$^{st}$ Strand Buffer

2 μL 0.1M DTT

1 μL 10 mM dNTP Mix

Create 2$^{nd}$ Strand conditions by adding

93 μL RNase free H$_2$O

30 μL 5×2$^{nd}$ Strand Buffer

3 μL 10 mM dNTP Mix

1 μL *E. coli* DNA Ligase (10 units/μL)

4 μL *E. coli* DNA Polymerase I (10 units/μL)

1 μL *E. coli* RNase H (2 units/μL)

Total 150 μL. Incubate 16° C. for 2 hours.

Add 2 μL T4 DNA Polymerase (10 units), 16° C., 5 minutes.

Add 10 μL 0.5M EDTA, place on ice.

Add 150 μL of Phenol:Choloroform:Isoamyl alcohol (25:24:1). Vortex thoroughly and centrifuge 14,000×g at room temperature for 5 minutes. Carefully remove the upper aqueous layer and transfer to a new tube.

Add 70 μL 7.5M NH$_4$OAC, 0.5 mL 100% ethanol (−20° C.), mix, centrifuge at 20,000×g, 4° C., 20 minutes. Carefully remove the supernatant.

The pellet is washed with 500 μL of 70% ethanol (−20° C.) and centrifuged at 20,000×g for 5 minutes. Remove supernatant carefully and dry.

Sal I Adapter Ligation (1) Pellet is resuspended in

25 μL RNase Free H$_2$O

10 μL 5×T4 DNA Ligase Buffer

10 ML Sal I Adapters

5 μL T4 DNA Ligase

Total 50 μL, 16° C., 16 hours.

Add 50 μL of Phenol:Choloroform:Isoamyl alcohol (25:24:1). Vortex thoroughly and centrifuge 14,000×g at room temperature for 5 minutes. Carefully remove the upper aqueous layer and transfer to a new tube.

Add 25 μL 7.5M NH$_4$OAC, 150 μL 100% ethanol (−20° C.), mix, centrifuge at 20,000×g, 4° C., 20 minutes. Carefully remove the supernatant.

The pellet is washed with 500 μL of 70% ethanol (−20° C.) and centrifuged at 20,000×g for 5 minutes. Remove supernatant carefully and dry.

Not I Digestion

To adapted cDNA add the following reagents:

41 μL RNase Free H$_2$O

5 μL React 3 Buffer

4 μL Not I

Total 50 µL, incubate 37° C. for 2–3 hours.

Add 50 µL of Phenol:Choloroform:Isoamyl alcohol (25:24:1). Vortex thoroughly and centrifuge 14,000×g at room temperature for 5 minutes. Carefully remove the upper aqueous layer and transfer to a new tube.

Add 25 µL 7.5M NH$_4$OAC, 150 µL 100% ethanol (−20° C.), mix, centrifuge at 20,000×g, 4° C., 20 minutes. Carefully remove the supernatant.

The pellet is washed with 500 µL of 70% ethanol (−20° C.) and centrifuged at 20,000×g for 5 minutes. Remove supernatant carefully and dry.

Separate cDNA from adapter by size fraction column

Place one of the cDNA size fractionation columns in a support. Remove the top cap first and then the bottom cap. Allow the excess liquid (20% ethanol) to drain.

Pipet 0.8 ml of TEN buffer [10 mM Tris-HCl (pH 7.5), 0.1 mM EDTA, 20 mM NaCl. Autoclaved] onto the upper frit and let drain completely. Repeat this step three more times for a total 3.2 ml.

Label 20 sterile microcentrifuge tubes from 1 to 20, and place them in a rack with tube 1 under the outlet of the column.

Add 97 µl of TEN buffer to the cDNA pellets and mix gently.

Add the entire sample to the center of the top fritz and let it drain into the bed. Collect the effluent into tube 1.

Add 100 µl of TEN buffer to the column and collect the effluent into tube 2.

Beginning with the next 100 µl aliquot of TEN buffer, collect single-drop (~35 µl) fraction into individual tubes. Continue adding 100 µl aliquots of TEN buffer until you have collected a total of 18 drops into tubes 3 through 20, one drop per tube.

Using an automatic pipet, measure the volume in each tube, use a fresh tip for each fraction to avoid cross-contamination. Record each value in column A. Identify the fraction for which the value in column is closest to, but not exceeding 550 µl.

Place the tubes in a scintillation counter and obtain Cerenkov counts for each fraction.

Based on cpm of each fraction, and total volume in column B (<550 µl), decide the fraction to be combined.

Add ½ volume 7.5M NH$_4$OAC, 5 µl 1 mg/ml yeast tRNA, followed by 3 volumes 100% ethanol, Vortex the mixture thoroughly, and centrifuge at 20,000×g, 4° C., 20 minutes. Carefully remove the supernatant.

Rinse the pellet gently with 200 µl 70% cold ethanol. Centrifuge for 2 min at 20,000×g and remove the supernatant.

Lyophilize the pellet for 5 min to evaporate residual ethanol.

Count the dry pellet to determine amount of cDNA yield.

Ligation and Transformation

Re-suspend cDNA pellet to a concentration of 5 ng/µl.

For each sample prepare a tube with

| | |
|---|---|
| 31 µl | ddw |
| 4 µl | 5 ng/ul cDNA (20 ng) |
| 1 µl | pSPORT1 vector (Sal I-Not I) (50 ng) |
| 5 µl | 10 × NEB T4 DNA ligase buffer |
| 5 µl | T4 DNA ligase |

Total 50 µl, incubate at 16° C. for overnight.

Dilute 1 µl of ligation into 9 µl dd.

Transform 1 µl of 1:10 dilution with 20 µl of DH-10B electrocompetent cells. Electroporate at 2.5 KV.

Recover cells in 1 mL SOC (pH 7.0, 22° C.). Incubate @ 37° C., 60 minutes, 250 rpm.

Plate 10 and 100 µl of transformation onto LB+2× Carbenicillin agar plates. Grow overnight at 37° C. and determine titer of ligation, titer per ng and titer per total amount of cDNA (titer/library).

Solutions and reagents needed

| Name | Company | Part No. |
|---|---|---|
| Taq DNA Polymerase | Amersham | T03031 |
| Cloned Pfu Polymerase | Stratagene | 600159-81 |
| Primers for eIF4E/eIF4G fusion protein construct | | |

(1) 5'-primer of 4E domain
5'-GAGATATACCATGGCGACTGTCGAACCGGA-3' (SEQ ID NO:01)

(2) 3'-Primer of 4E domain
5'-AGTTAAGTGGGCACCTGGTCTTTGAGAATCTTCTCTGGAGACAGCAACAAACCTATTTTTAG-3'
(SEQ ID NO:02)

(3) 5'-Primer of 4G domain
5'-GCTGTCTCCAGAGAAGATTCTCAAAGACCAGGTGCCCACTTAACTGTGAAAAGGAGACGGAAAA
TTAAGGAG-3' (SEQ ID NO:03)

(4) 3'-Primer of 4G domain
5'-GCCGGATCCTCGAGTCATTACTTATCGTCATCGTCCTTGTAATCGCCAAGGTTGG
CAAAGGATGG-3' (SEQ ID NO:04)

| | | |
|---|---|---|
| SeaKem GTG Agarose | FMC | 50074 |
| SeaKem LE Agarose | FMC | 50004 |
| QIAquick Gel Extraction Kit | QIAGEN | 28704 |
| Nco I | NEB | 193L |
| Ban I | NEB | 118L |
| Xho I | NEB | 146L |
| pET15b Expression Kit | Novagen | 69668-3 |

-continued

Solutions and reagents needed

| Name | Company | Part No. |
|---|---|---|
| T4 DNA Ligase | NEB | 202L |
| ElectroMAX DH10B cells | Gibco-BRL | 18290-015 |
| QIAGEN Plasmid Midi Kit | QIAGEN | 12143 |
| 7-methylguanosine 5 = triphosphate immobilized on Sepharose 4B | Sigma | M-4648 |
| 7-methylguanosine 5 = triphosphate, Sodium Salt | Sigma | M-6133 |
| Tris/Glycine/SDS Buffer | BioRad | 161-0732 |
| Laemmli Sample Buffer | BioRad | 161-0737 |
| SDS-Broad Range Standard | BioRad | 161-0317 |
| Coomassie Stain Solution | BioRad | 161-0436 |
| Destain Solution, Coomassie R-250 | BioRad | 161-0438 |
| Slide-A-Lyzer 2,000 MWCO Dialysis Cassette | Pierce | 66210 |
| Coomassie Plus-200 Protein Assay Reagent | Pierce | 23238 |
| TransProbe T Kit | Pharmacia biotech | 27-9276-01 |
| Millipore Microcon 10,000 MWCO Microconcentrator | Millipore | 42422 |
| EZ-LINK NHS-LC-LC-Biotin | Pierce | 21343 |
| ImmunoPure HABA | Pierce | 28050 |
| Dynabeads M280 StreptAvidin | Dynal | 112.06 |
| SUPERSCRIPT Plasmid System for cDNA Synthesis and Plasmid Cloning | Gibco-BRL | 18248-013 |
| RNase ONE Ribonuclease | Promega | M4261 |

It is evident from the above results and discussion that improved methods for isolating full length mRNAs are provided. With the subject methods, one can obtain a population of full length mRNAs from an initial sample, where shorter mRNA fragments are removed. In addition, one can employ the subject methods to obtain a library of substantially full length cDNAs. Finally, the subject fusion proteins provide for greater binding specificity to the 5' cap structure than is achieved with other protocols, thereby improving the obtainable results. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid comprising a sequence encoding a fusion protein, which fusion protein comprises an eIF-4E domain and an eIF-4G domain joined by a linker domain.

2. A host cell comprising a nucleic acid according to claim 1.

3. The nucleic acid of claim 1, wherein the linker domain is a flexible linking domain.

4. The nucleic acid of claim 1, wherein the fusion protein has a binding affinity for a 5' cap structure of a nucleic acid greater than a binding affinity of eIF-4E for the 5' cap structure.

5. The nucleic acid of claim 1, wherein the fusion protein further comprises a ligand domain.

6. A vector comprising the nucleic acid according to claim 1.

* * * * *